(12) United States Patent
Shearer

(10) Patent No.: US 12,304,885 B2
(45) Date of Patent: May 20, 2025

(54) SYNTHESIS AND PURIFICATION OF CBDA

(71) Applicant: The Regents of the University of Colorado, Denver, CO (US)

(72) Inventor: Randall L. Shearer, Broomfield, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 18/856,957

(22) PCT Filed: Apr. 20, 2023

(86) PCT No.: PCT/US2023/019207
§ 371 (c)(1),
(2) Date: Oct. 15, 2024

(87) PCT Pub. No.: WO2023/205298
PCT Pub. Date: Oct. 26, 2023

(65) Prior Publication Data
US 2025/0115542 A1    Apr. 10, 2025

Related U.S. Application Data

(60) Provisional application No. 63/363,252, filed on Apr. 20, 2022.

(51) Int. Cl.
*C07C 51/573*    (2006.01)
(52) U.S. Cl.
CPC .................... *C07C 51/573* (2013.01)
(58) Field of Classification Search
CPC .................................... C07C 51/573
See application file for complete search history.

(56) References Cited

U.S. PATENT DOCUMENTS

| | | |
|---|---|---|
| 2016/0228385 A1 | 8/2016 | Sievers et al. |
| 2019/0359550 A1 | 11/2019 | Wohleb et al. |
| 2021/0309629 A1 | 10/2021 | Durst et al. |
| 2022/0079880 A1 | 3/2022 | Piccariello et al. |

OTHER PUBLICATIONS

Caprioglio D, Mattoteia D, Pollastro F, Negri R, Lopatriello A, Chianese G, Minassi A, Collado JA, Munoz E, Taglialatela-Scafati O, Appendino G. The Oxidation of Phytocannabinoids to Cannabinoquinoids. J Nat Prod. May 22, 2020;83(5):1711-1715. doi: 10.1021/acs.jnatprod.9b01284. Epub Apr. 21, 2020. PMID: 32315173; PMCID: PMC7997633.

Goerl B, Watkins S, Metcalf C, Smith M, Beenhakker M. Cannabidiolic acid exhibits entourage-like improvements of anticonvulsant activity in an acute rat model of seizures. Epilepsy Res. Jan. 2021;169:106525. doi: 10.1016/j.eplepsyres.2020.106525. Epub Dec. 3, 2020. PMID: 33310415; PMCID: PMC7855831.

Nahar L, Uddin SJ, Alam MA, Sarker SD. Extraction of naturally occurring cannabinoids: an update. Phytochem Anal. May 2021;32(3):228-241. doi: 10.1002/pca.2987. Epub Sep. 7, 2020. PMID: 32893413.

Puleo TR, Sujansky SJ, Wright SE, Bandar JS. Organic Superbases in Recent Synthetic Methodology Research. Chemistry. Mar. 1, 2021;27(13):4216-4229. doi: 10.1002/chem.202003580. Epub Jan. 12, 2021. PMID: 32841442.

Sadamitsu Y, Okumura A, Saito K, Yamada T. Kolbe-Schmitt type reaction under ambient conditions mediated by an organic base. Chem Commun (Camb). Aug. 13, 2019;55(66):9837-9840. doi: 10.1039/c9cc04550c. PMID: 31364638.

*Primary Examiner* — Sikarl A Witherspoon
(74) *Attorney, Agent, or Firm* — McGaw Law, P.C.; Michael M. McGaw

(57) ABSTRACT

Methods and systems for the preparation of high purity and high quality cannabinoid acids and metal salts of cannabinoids. Cannabidiolic acid (CBDA) is a major cannabinoid of interest for and health reasons. It is the natural precursor for cannabidiol (CBD). The invention provides methods for the synthesis of CBDA from CBD with reagents that produce a high purity product without need for further purification. Insertion of a magnesium complexing agent prior to conversion of the reaction intermediate to the final acid product produces a high purity product with aesthetically pleasing white color and neutral odor. Methods are provided for the simultaneous synthesis and purification of cannabinoid acids, especially CBDA, produced from high purity CBD (or other cannabinoid) via a Kolbe-Schmitt type reaction using an organic base, such as DBU (1,8-diazabicyclo[5.4.0]undec-7-ene), incorporating complexation of acid anions to a multivalent metal, alkaline earth or transition metal, prior to product acid work-up. During the work-up to the final acid, the distinct solubility of the complex in selected solvents is used advantageously to first exclude water soluble reagents and impurities and next to exclude lipophilic hydroxyl-quinone impurities, as well as any unconverted CBD.

29 Claims, 2 Drawing Sheets

Reactions (1) CBD $\xrightarrow[\text{DBU, RT 24 hours}]{\text{Press. } CO_2 \text{ ACN}}$ DBU-CBDA Complex (2) DBU-CBDA Complex $\xrightarrow{\text{Anh. } Mg(SO_4)}$ $(CBDA)_2$-Mg (3) $(CBDA)_2$-Mg $\xrightarrow{\text{MeOAc, HCl}}$ CBDA (Net 4) CBD + $CO_2$ → CBDA

SYNTHESIS AND PURIFICATION OF CBDA

CROSS-REFERENCE TO RELATED APPLICATIONS

This application claims the benefit of U.S. Provisional Application No. 63/363,252 filed Apr. 20, 2022.

FIELD OF INVENTION

The invention relates to methods of preparing cannabidiolic acid and other cannabinoid acids in substantially pure form.

BACKGROUND OF THE INVENTION

It is desirable to have very pure cannabinoids for research purposes and for the purpose of blending products to accurately known levels of cannabinoids, such as for nutraceutical or therapeutic reasons. Cannabinoid acids (CA) in general, and cannabidiolic acid (CBDA) in specific, are of particular interest, but unfortunately are frequently lost during extraction due to their unstable nature. On the other hand, high purity cannabidiol (CBD) is readily obtained from hemp (*cannabis* that contains less than 0.3 mass % Delta9-THC) in isolate form commonly following the steps of solvent maceration, winterization, distillation and crystallization. Unfortunately, it is not possible to isolate CBDA in the same manner as CBD because CBDA does not readily crystalize and, at the high temperatures required for distillation, cannabinoid acids undergo decarboxylation forming the neutral cannabinoid, e.g., CBD in the instance of CBDA.

SUMMARY OF THE INVENTION

The present invention provides methods and systems for the preparation of high purity and high quality CBDA. CBDA is a major cannabinoid of interest for therapeutic and health reasons. It is the natural precursor of CBD. The invention provides methods for the synthesis of CBDA from CBD with reagents that produce a high purity product without need for further purification. In addition, the methodology taught herein can be used to produce a variety of highly pure cannabinoid acids and/or metal salts of cannabinoids from corresponding cannabinoids (e.g., one can produce a highly pure cannabigerolic acid (CBGA) from a cannabigerol (CBG) starting material).

Prior methods for the production of CBDA often utilized complicated separations, e.g., via chromatography. The present invention provides for the formation of cannabinoid acids from the corresponding neutral cannabinoid and simplifies the formation of cannabinoid acid metal salts without cannabinoid acid isolation. Instead, the present invention teaches the direct formation of metal salts after complexation with an organic base/cannabinoid carboxylate complex. Then pure cannabinoid acids (natural or synthetic) are isolated via acidification of the metal salt. The present invention overcomes the problem of formation of oxidation byproducts that are base catalyzed. One approach to the production of CBDA would include the use of crystallization to purify the cannabinoid acid salts to exclude impurities, such as those base catalyzed oxidation byproducts. The present invention minimizes the formation of base-catalyzed oxidation byproducts in the first place and reduces their concentrations further through selection of solvents that wash them from precipitated metal salts of the cannabinoid acids.

Insertion of a magnesium complexing agent prior to conversion of the reaction intermediate to the final acid product produces a high purity product with aesthetically pleasing white color and neutral odor. In contrast, naturally extracted CBDA contains numerous impurities that impart undesirable odor and color. The nature of the colored impurities make it very difficult to produce a high purity product without costly purification steps.

The present invention provides a method or methods for simultaneous synthesis and purification of cannabinoid acids, especially CBDA (cannabidiolic acid), produced from high purity CBD (cannabidiol) via a Kolbe-Schmitt type reaction using an organic base, such as DBU (1,8-diazabicyclo[5.4.0]undec-7-ene), incorporating complexation of acid anions to a multivalent metal, alkaline earth or transition metal, prior to product acid work-up. During the work-up to the final acid, the distinct solubility of the complex in selected solvents is used advantageously to first exclude water soluble reagents and impurities and next to exclude lipophilic hydroxyl-quinone impurities, as well as any unconverted CBD.

The methodology also provides compounds of the aforementioned alkaline earth and transition metal cannabinoid acid salts. These may also be solvent washed to remove impurities. The method produces exceptionally high purity cannabinoid acids, such as CBDA, in concentrations >99% by mass, that are free of objectionable off-odors and colors. The cannabinoid acid salts will be useful as pharmaceutical and nutraceutical ingredients that provide for the benefits of cannabinoid acids in addition to dietary supplementation of trace metal nutrients, including calcium, magnesium and zinc. Further advantages of the present methodologies include lower costs of production and higher quality.

In a first aspect the present invention provides a method for the synthesis and purification of cannabidiolic acid (CBDA), or, more particularly, a metal salt of cannabidiolic acid. The method of the first aspect can include the steps of dissolving cannabidiol (CBD) in acetonitrile, adding 1,8-diazabicyclo[5.4.0]undec-7-ene (DBU) to the dissolved CBD to form a first reaction mixture, incubating the first reaction mixture at 15 to 25° C. under a pressure of 24 to 36 bar carbon dioxide for about 1 hour to about 48 hours (preferably about 18 to about 30 hours; most about preferably about 24 hours) to form a complex between DBU and CBDA, mixing the DBU-CBDA complex with anhydrous magnesium sulfate to form a second reaction mixture comprising $Mg(CBDA)_2$; and precipitating $Mg(CBDA)_2$ from the second reaction mixture using normal pentane to form a metal salt of CBDA, where it is understood that the metal is in a complexed cation form and the CBDA is in a complexed anion carboxylate form.

In certain embodiments the method further includes the steps of acidifying the metal salt of CBDA with hydrochloric acid and precipitating the formed acid with methyl acetate to yield a purified cannabidiolic acid. The acidifying and precipitating steps are performed at about 25° C. or less. In an advantageous embodiment of the first aspect, no additional steps affecting the general nature of the process will be required to form the high quality CBDA or the metal salt of the CBD.

In a second aspect the present invention provides a method for the synthesis and purification of a cannabinoid acid and/or a metal salt of a cannabinoid acid. The method can include the steps of (1) dissolving a cannabinoid in an aprotic polar solvent (e.g., acetonitrile); (2) adding 1,8-diazabicyclo[5.4.0]undec-7-ene (DBU) to the dissolved CBD to form a first reaction mixture; (3) incubating the reaction mixture at low temperature under high pressure carbon dioxide for one or more hours (e.g., about 1 to about 48 hours; more preferably about 12 to about 30 hours; most preferably about 24 hours) to form a complex between DBU and the cannabinoid acid anion; (4) mixing the DBU-cannabinoid acid (anion) complex with anhydrous magnesium sulfate to form a second reaction mixture; and (5) precipitating Mg(cannabinoid acid anion)$_2$ from the second reaction mixture using an organic solvent to form a metal salt of the cannabinoid. As an alternative to DBU, other strong bases could be used. These include 1,5,7-Triazabicyclo(4.4.0)dec-5-ene (TBD), 7-Methyl-1,5,7-triazabicyclo(4.4.0)dec-5-ene (MTBD), 1,5-Diazabicyclo[4.3.0]non-5-ene (DBN), and 1,1,3,3-Tetramethylguanidine (TMG). Organic superbases are discussed by Puleo et al. [Puleo T R, Sujansky S J, Wright S E, Bandar J S. Organic Superbases in Recent Synthetic Methodology Research. Chemistry. 2021 Mar. 1; 27(13):4216-4229. doi: 10.1002/chem.202003580. Epub 2021 Jan. 12. PMID: 32841442.], the contents of which are incorporated by reference. DBU is deemed to be an advantageous base due to its low cost and effectiveness in achieving the desired product(s).

The method of the second aspect can further include the step of acidifying the metal salt with a mineral acid and a solvent, such as methyl acetate, to form a purified cannabinoid acid. More particularly, the method can further include the step of acidifying the metal salt with HCl and methyl acetate, to form a purified cannabinoid acid. In an advantageous embodiment the low temperature is about 15 to 25° C. In further advantageous embodiments the incubation period is about 12 hours to about 30 hours. In a particularly advantageous embodiment the incubation period is about 24 hours. The incubation can be performed in a pressure vessel at about 24 to 36 bar; advantageously 30 bar. An advantageous aprotic polar solvent is acetonitrile. Contemplated alternatives to acetonitrile include dimethyl sulfoxide, sulfolane, N,N-dimethylacetamide. The organic solvent used to precipitate the metal salt can be normal pentane, normal hexane, methyl acetate or ethyl acetate. It is contemplated that carbonyl sulfide (OCS) and carbon disulfide (CS2) can be explored as alternatives to carbon dioxide used in the third step.

In a third aspect the present invention provides a method for the synthesis and purification of a cannabinoid. The method can include the steps of (1) dissolving the cannabinoid in aprotic polar solvent (e.g., acetonitrile); (2) adding 1,8-diazabicyclo[5.4.0]undec-7-ene (DBU) to the dissolved cannabinoid to form a first reaction mixture; (3) incubating the reaction mixture at low temperature under high pressure carbon dioxide for a plurality of hours to form a complex between DBU and the cannabinoid; (4) mixing the DBU-cannabinoid complex with anhydrous magnesium sulfate to form a second reaction mixture; and (5) precipitating Mg(cannabinoid acid)$_2$ from the second reaction mixture using an organic solvent to form a metal salt of the cannabinoid acid. The cannabinoid used in the method according to the third aspect can be CBD, CBG, CBN, or THC. As an alternative to DBU, other strong bases could be used. These include 1,5,7-Triazabicyclo(4.4.0)dec-5-ene (TBD), 7-Methyl-1,5,7-triazabicyclo(4.4.0)dec-5-ene (MTBD), 1,5-Diazabicyclo[4.3.0]non-5-ene (DBN), 1,1,3,3-Tetramethylguanidine (TMG). The method of the third aspect can further include the step of acidifying the metal salt with a mineral acid and a solvent, such as methyl acetate, to form a purified cannabinoid acid. More particularly, the method can further include the step of acidifying the metal salt with HCl and methyl acetate, to form a purified cannabinoid acid. In an advantageous embodiment the low temperature is about 15 to about 25° C. In further advantageous embodiments the incubation period is about 12 hours to about 30 hours. In a particularly advantageous embodiment the incubation period is about 24 hours. The incubation can be performed in a pressure vessel at about 24 to 36 bar; advantageously bar. An advantageous aprotic polar solvent is acetonitrile. Contemplated alternatives to acetonitrile include dimethyl sulfoxide, sulfolane, N,N-dimethylacetamide. The organic solvent used to precipitate the metal salt can be normal pentane, normal hexane, methyl acetate or ethyl acetate. It is contemplated that carbonyl sulfide (OCS) and carbon disulfide (CS2) can be explored as alternatives to carbon dioxide used in the third step.

According to some embodiments, the cannabinoid compound used to prepare the CBDA according to the invention is present in one or more extracts of a *cannabis* plant. According to some embodiments, the *cannabis* plant extract is obtained from a strain selected from the group consisting of *Cannabis sativa, Cannabis* indica, *Cannabis ruderalis*, a hybrid strain, and combinations thereof. According to some embodiments, the *cannabis* plant extract is obtained from a strain selected from the group consisting of a high-CBD strain, a high-THC strain, and a combination thereof. According to some embodiments, the *cannabis* plant extract comprises at least one cannabinoid selected from the group consisting of cannabidiol (CBD), tetrahydrocannabinol (THC), cannabinol (CBN), cannabigerol (CBG), cannabichromene (CBC), acids thereof and combinations thereof.

The present invention provides a purified CBDA. The purified CBDA may be included as a component of a pharmaceutically acceptable composition for administration to a patient for a therapeutic effect in treatment of a disorder. In one embodiment, the pharmaceutically acceptable compositions of the invention may include CBDA in an amount above the placebo effect (including homeopathic compositions), up to and including 99 wt % pure CBDA. In specific embodiments, the compositions comprise about 1 to 90 wt %, 1 to 80 wt %, 10 to 70 wt %, 15-60 wt %, 20-60 wt %, or 25-50 wt % IBDA. The compositions may be in any conventional administration form, including solid unit dosage forms such as tablets, wafers, pellets, lozenges, solutions (for example, in water or ethanol), salves, creams, lotions, and the like, and may contain conventional additives, including pharmaceutical carriers, excipients, and the like.

The extracts, compositions and products of the invention may be administered to a mammal (e.g., human, rat, mouse, monkey, dog, cat, horse, etc.) for any one of various therapeutic effects for which CBD and/or CBDA are known in the art. In this regard, the extracts, compositions and products of the invention may be administered to provide anti-oxidant, antiseizure, neuroprotective, anti-inflammatory, analgesic, anti-tumor, anti-stress, anti-psychotic, and/or anti-anxiety properties, among others. Treatment of multiple sclerosis, Parkinson's disease, alcohol abuse, tumor metastasis, stress, including, post-traumatic stress disorders, migraines, pain, concussion, anxiety, diabetes, and the like may be treated with the extracts, compositions and products of the invention.

According to some aspects, the present invention provides a pharmaceutical composition is for use in the treatment of a disease, disorder or symptom amenable to treatment with a cannabinoid acid (CA).

According to another aspect, the present invention provides a pharmaceutical composition comprising a therapeutically effective amount of a compound represented by the structure of CBDA as defined herein, and a pharmaceutically acceptable carrier or excipient. Pharmaceutically acceptable carriers or excipients comprise at least one of a binder, a filler, a diluent, a surfactant or emulsifier, a glidant or lubricant, a buffering or pH adjusting agent, a tonicity enhancing agent, a wetting agent, a preservative, an antioxidant, a flavoring agent, a colorant, and a mixture or combinations thereof.

According to some embodiments, the pharmaceutical composition is in a form selected from the group consisting of tablet, pill, capsule, pellets, granules, powder, a wafer, coated or uncoated beads, lozenge, sachet, cachet, elixir, a depot system, a patch, suspension, dispersion, emulsion, solution, syrup, aerosol, oil, ointment, suppository, a gel, and a cream.

According to some embodiments, the pharmaceutical composition is for use in the treatment of a disease, disorder or symptom amenable to treatment with a cannabinoid acid (CA).

According to another aspect, the present invention provides a pharmaceutical composition comprising a therapeutically effective amount of a cannabinoid acid (CA) for use in the treatment of a disease, disorder or symptom amenable to treatment with CA.

The disease, disorder or symptom amenable to treatment with CBDA is selected from the group consisting of pain, autoimmune disease, cancer, bacterial infection, impaired neurological function, inflammation, nausea, vomiting, convulsions, low appetite and glaucoma.

According to some embodiments, the pharmaceutical composition is for use in the treatment of pain.

According to some embodiments, the pharmaceutical composition is for use in the treatment of autoimmune disease.

According to some embodiments, the pharmaceutical composition is for use in the treatment of cancer.

According to some embodiments, the pharmaceutical composition is for use in the treatment of bacterial infection.

According to some embodiments, the pharmaceutical composition is for use in the treatment of impaired neurological function.

According to some embodiments, the impaired neurological function is selected from the group consisting of stroke, trauma, Parkinson's Disease, vascular dementia, senile dementia, Alzheimner's disease, mild cognitive impairment, Huntington's Disease, Amyotrophic lateral sclerosis (ALS), epilepsy, multiple sclerosis, and psychiatric disorders. Each possibility represents a separate embodiment of the present invention.

According to some embodiments, the impaired neurological function is epilepsy.

According to some embodiments, the impaired neurological function is a psychiatric disorder.

According to some embodiments, the psychiatric disorder is selected from the group consisting of depression, anxiety, acute or chronic stress, schizophrenia, panic attacks, ADHD-11), bipolar disorder, obsessive compulsive disorder and personality disorders. Each possibility represents a separate embodiment of the present invention.

According to some embodiments, the pharmaceutical composition is for use in the treatment of an inflammation. According to some embodiments, the pharmaceutical composition is for use in treating joint inflammatory diseases and joint degeneration. According to additional embodiments, the pharmaceutical composition is for use in treating respiratory inflammation. According to additional embodiments, the pharmaceutical composition is for use in treating inflamatory bowel disease.

According to some embodiments, the pharmaceutical composition is for use in the treatment of nausea, vomiting or low appetite.

According to some embodiments, the pharmaceutical composition is for use in the treatment of convulsions.

According to some embodiments, the pharmaceutical composition is for use in the treatment of glaucoma.

According to some embodiments, the pharmaceutical composition is for use in the treatment of gastrointestinal diseases or disorders.

According to some embodiments, the disease, disorder or symptom amenable to treatment with CBD is selected from the group consisting of Non-Alcoholic Fatty Liver Disease (NAFLD), chronic kidney disease (CKD), obesity, hyperglycemia, diabetes, metabolic syndrome and/or obesity related diseases.

According to some embodiments, the pharmaceutical composition is for use in the treatment of obesity. According to some embodiments, the pharmaceutical composition is for use in the treatment of muscular dystrophy.

Generally speaking, in the overall reaction a suitable strong organic base and neutral cannabinoid are combined to form the generic base-cannabinoid acid salt complex. Then, the precipitating metal will be one that forms insoluble hydroxides, like Mg, Ca, Zn and others.

BRIEF DESCRIPTION OF THE DRAWINGS

For a fuller understanding of the invention, reference should be made to the following detailed description, taken in connection with the accompanying drawing, in which.

DETAILED DESCRIPTION OF THE PREFERRED EMBODIMENT

Figure 1:
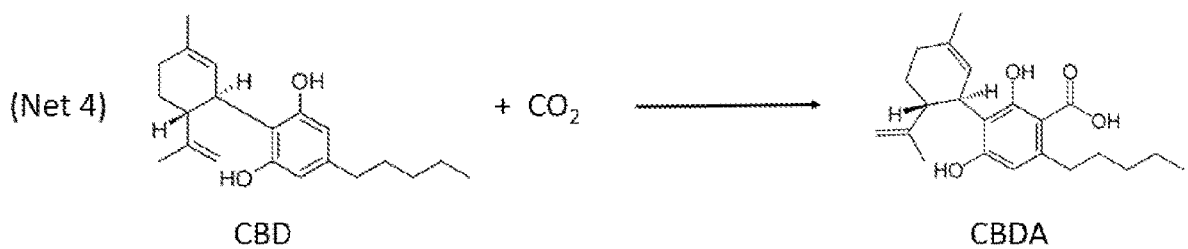
FIG. 1 is a drawing illustrating a series of reactions using the outlined chemical steps to produce a high quality and low-cost CA/CBDA.
Figure 2:
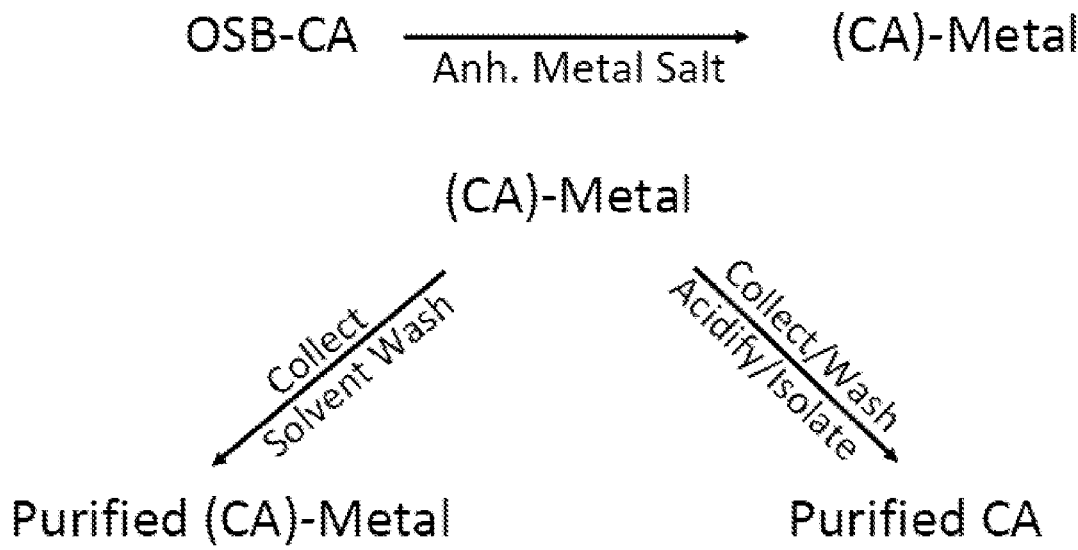
FIG. 2 is a drawing illustrating cannabinoid acid complexes. This figure illustrates that the intermediate metal salt of the cannabinoid acid is readily isolated as the pure salt, or alternatively through washing, acidification and isolation, a pure cannabinoid acid is obtained.

Extraction of cannabinoid acids from hemp requires the application of a relatively low temperature and expensive processes, such as preparative chromatograph techniques, aqueous extraction in high pH caustic media [U.S. Patent Application Pub. No. 2019/0359550A1], and via complex liquid-liquid and liquid-solid extraction techniques, or high pressure supercritical fluid techniques, all of which produce large quantities of byproduct solvents that have to be reclaimed or disposed of [Nahar, L, Uddin, S J, Alam, M A and Sarker, S D, "Extraction of naturally occurring cannabinoids: An update," *Phytochemical Analysis*, 2020, 32 (3) pp 228-241; U.S. Patent Application Pub. No. US 2016/0228385A1]. Unfortunately, such extraction techniques suffer from a number of shortcomings in addition to being complex and expensive. They contain a mixture of cannabinoid acids that occur naturally within hemp because the above techniques extract all acids similarly. Other impurities also naturally occurring in hemp include, terpenes, flavonoids, waxes, fatty acids, and sugars that will be extracted to varying degrees and will lessen the purity of desired cannabinoid acid products. Further, during extraction, oxidation of cannabinoids leads to formation of a class of compounds known as hydroxyl-quinones, which are highly colored active species [Caprioglio, Diego et al. "The Oxidation of Phytocannabinoids to Cannabinoquinoids." Journal of natural products vol. 83, 5 (2020): 1711-1715]. These are particularly troublesome in processes that use bases, leading to high pH conditions. Remarkably, even though the method taught herein can utilize a very high pH organic base, the unique characteristics of the intermediate metal acid complexes allow those impurities to be removed.

It is desirable to have very pure cannabinoids for research purposes in addition to being able to blend products to accurately known levels of cannabinoids, e.g. for nutraceutical or therapeutic reasons. Cannabinoid acids are of particular interest but unfortunately are frequently lost during extraction due to their unstable nature. On the other hand, high purity CBD is readily obtained from hemp (cannabis that contains less than 0.3 mass % Delta9-THC) in isolate form commonly following steps of solvent maceration, winterization, distillation and crystallization. Unfortunately, it is not possible to isolate CBDA in the same manner because CBDA does not readily crystalize and, at the high temperatures required for distillation, cannabinoid acids undergo decarboxylation forming the neutral cannabinoid, e.g., CBD in the instance of CBDA.

All of these problems lead to the cannabinolic acids being relatively rare and valuable compared to their neutral counterparts.

The series of reactions shown in the figure outline chemical steps used in this inventive process. In the first step (1) CBD is reacted at low temperature with DBU under high pressure carbon dioxide in the presence of an aprotic polar solvent, such as acetonitrile, within a pressure vessel for several hours. A complex between DBU and CBDA is formed. Instead of using an acid to liberate the cannabinolic acid CBDA, in step (2) an excess of an anhydrous metal salt is used to form and precipitate a metal CBDA salt, in this case magnesium sulfate was used. An excess of metal salt helps to drive precipitation reaction to completion by leading to solubility limits of the cannabinoid acid salt being exceeded. The anion of the salt could help remove residual DBU. Because the metal salts are relatively inexpensive compared to the desired products, use of a 5-fold or even 10-fold excess is reasonable. It is contemplated that other anhydrous metal salts could be used. The metal cation of the salt should be one that forms an insoluble hydroxide in water. Contemplated anhydrous metal salts include magnesium salts including magnesium acetate, magnesium chloride, magnesium nitrate, and magnesium sulfate; calcium salts including calcium acetate, calcium chloride, calcium nitrate, and calcium sulfate; strontium salts including strontium acetate, strontium chloride, and strontium nitrate, bismuth salts including bismuth chloride and bismuth sulfate; iron (II) salts including ferrous acetate and ferrous sulfate; iron(III) salts including ferric nitrate and ferric sulfate; cobalt salts including cobalt acetate, cobalt chloride, cobalt nitrate and cobalt sulfate; and zinc salts including zinc acetate, zinc chloride, zinc nitrate, and zinc sulfate. To make the magnesium salt of a cannabinoid acid, the magnesium source (reagent) can consist of a simple anhydrous magnesium salt of readily exchangeable anions, such as sulfate, nitrate, chloride. This would be the same with other metals, e.g., calcium, zinc, iron, copper, bismuth, cobalt, etc. The metal itself must be capable of forming a strong bond, e.g., a chelated complex with the cannabinoid acid anion. Conversely, it is desired to use a non-metal anion that is readily soluble in water. Water is used to remove reagents and water-soluble impurities. The metal salt precipitate is collected and dried and washed with an organic solvent such as normal pentane, normal hexane, methyl acetate or ethyl acetate. Surprisingly, the metal acid salt is not soluble to an appreciable amount in any of these solvents, however, unreacted CBD and hydroxyl quinones are readily soluble and thus removed from the intermediate metal salt product. The process may be stopped at this point if the metal salt of the cannabinoid is desired.

If the highly pure cannabidiolic acid (CBDA) is desired, then the metal salt is acidified with a mineral acid and a solvent, such as methyl acetate, is used to separate the formed acid from the aqueous solution, which now contains metal ions along with the mineral acid counter anion. Many strong mineral acids can be used, such as hydrochloric acid, sulfuric acid, nitric acid. Hydrochloric acid is preferable because it is inexpensive and salts of it are generally non-toxic. Solvents for this step need to be able to dissolve CBDA and need to be water insoluble, such that the solvent aids in separation of the cannabinoid acid from starting materials and water. Other solvent choices could include ethyl acetate, methylene chloride, chloroform, n-pentane and other paraffin solvents. The more volatile the solvent the better, because this aids in its removal from the product.

The generation of highly pure cannabidiolic acid is shown as step (3) of the FIG. 1. The net reaction taken to completion is shown as reaction (4) in FIG. 1.

With further reference to FIG. 1, the low temperature for the first reaction (reaction 1) is generally about 15 to 25° C. Higher temperatures can speed up reaction 1, though around room temperature is very convenient because neither external cooling or heating would be required. Also 24 hours is a convenient reaction time for carrying out batch processes. In a continuous production process then it might be desirable to explore speeding up reaction 1. For reaction 2, some optimization might be desirable to maximize yield of the desired product, which could include adjusting the temperature and the time. Reaction 3 suffers at higher temperatures because the reverse reaction begins to occur (decarboxylation). So operating reaction 3 at or below 30° C. is important.

Operating a reaction at around room temperature is preferable if possible because neither heating nor cooling is required. All three reaction steps of the invention desirably work at room temperature. It might be possible to speed up reaction 1 by increasing reaction temperature higher than 35 or 40° C. The reaction time of about 24 hours is a convenient time and practically not that long. Reaction 1 is the only reaction that is not rapid. A time of about 20-24 hours produces good yields while extending to about 48 hours didn't increase yield, but also had no negative impact (other than longer reaction time).

Some study of temperature optimization of reaction 2 would be desirable because of there might be an optimum in terms of yield and selectivity to the desired product, i.e., minimizing unwanted impurities. Reaction 3 should be carried out at room temperature or below because heat causes the decarboxylation of cannabinoid acids (the reverse reaction).

With regard to the pressure used for the reaction(s), the higher the pressure, the greater the driving force for $CO_2$ to go into solution. The effect of this is to speed up the reaction. Room temperature for the reactions should prove effective [Sadamitsu, et al., "Kolbe-Schmitt type reaction under ambient conditions mediated by an organic base," *Chemical Communications,* 2019, Issue 66, pp. 9735-9882.]. At lower pressures, the size of the required reaction vessel increases because less mass of $CO_2$ is present per unit volume. Especially for large volume production, then the pressure used will directly impact the cost of process vessels, so all things being equal the higher the pressure the better, though one would prefer not to require pumps. Accordingly, an upper pressure limit would be about 1000 psi (~74 bar), while a practical lower pressure is about 100 psi (~7 bar).

The value of metal-cannabinolic acid salts is not well-known and appreciated, but research is uncovering potential significant uses. For example, a magnesium-infused CBDA (Mg-CBDa) was found to demonstrate anti-convulsive properties similar to CBD [Goerl, B., Watkins, S., Metcalf, C., Smith, M., and Beenhakker, M., "Cannabidiolic acid exhibits entourage-like improvements of anticonvulsant activity in an acute rat model of seizures," *Epilepsy Research*, Volume (2021) 169]. The material for this study was provided by Synthonics, Inc., [see e.g., U.S. Patent Application Pub. No. 2022/0079880A1].

Example:

While this example concerns the production of CBDA, the chemistry described below is applicable to multiple cannabinoids, e.g., cannabigerol (CBG), cannabinol (CBN), tetrahydrocannabinol (THC), etc., for conversion to their corresponding acids. In other words, it is contemplated that cannabinoids such as CBG, CBN, THC, etc., could be used as the starting material for the production of CBGA, CBNA and THCA, respectively, using the techniques, methodologies and other reagents taught herein.

About 13.5 g of high purity CBD was used as the starting material. It was dissolved in about 40 mL of acetonitrile and placed in a glass beaker placed within a pressure vessel. Just prior to sealing the vessel, 19 mL of DBU was added to the glass beaker and the pressure vessel was sealed. The vessel was charged with approximately 30 bar and set aside at room temperature for about 24 hours.

The pressure chosen depends on multiple factors, including the size of reactions vessels and the mass of reactants in that vessel. At an absolute minimum, the pressure should be greater than ambient pressure in order to help prevent atmospheric intrusion, and the mass of carbon dioxide, for example as determined by the ideal gas equation, needs to be sufficient to react with all of the cannabinoid and base. Practically, carbon dioxide is very inexpensive, so an excess is used, such as a 10-fold excess or more. Pressure above atmospheric pressure is readily obtained from carbon dioxide cylinders and 2-bar pressure is a lower range. At room temperature the pressure in carbon dioxide cylinders is nominally 60 bar and both liquid and gaseous carbon dioxide are present. The carbon dioxide can be added to the reaction vessel at up to this pressure without having to use a compressor/pump. There could be reasons why this might be advantageous to raise the pressure beyond 2 bar (e.g., faster reaction, higher solubility of reactants and products in the reaction mixed due to carbon dioxide being in or approaching supercritical conditions), such as is demonstrated herein.

After 24 hours, the vessel was slowly vented of carbon dioxide, opened, and approximately 15 g of anhydrous magnesium sulfate, using a glass rod, was stirred into the somewhat pinkish reaction mixture liquid. About 20 mL of normal pentane was added to the top of the mixture. A precipitate began to form in the bottom of the beaker and with stirring about 20 to 30 mL of distilled water was added. The mixture became warm and more white precipitate formed. A yellow organic layer on the top of the mixture was removed and discarded.

A 24-hour reaction time has been found to produce good yields. The minimum time (for complete or maximum conversion) can be established through experimental optimization, and will depend upon factors including the pressure and temperature of the reaction. Twenty-four hours is a convenient time that has been found to produce good yields. It is submitted that conditions could be optimized to be effective at the one-hour scale or perhaps even less. Longer times (e.g., in excess of 48 hours) would likely not increase yields and would require monitoring/controlling reactions for longer times, which uses more resources.

Low molecular weight alkanes, such as normal pentane, work well for the step 2 precipitation. A solvent can be chosen where the starting cannabinoid is soluble but one that is not very soluble in the polar solvent. So, isomers of propane, butane, pentane, hexane and heptane isomers are good choices, although propane and butane would require operation at high pressure in order to keep them in the liquid state.

A slightly pink-white solid was collected on filter paper in a Buchner funnel and was washed multiple times with water. After air drying for several hours the raw magnesium salt amounted to about 20 g indicating a high reaction yield. This product undoubtedly also contained bound water and some residual DBU, which is not of importance if the cannabinoid acid is the desired end product as both water and DBU will be separated from the cannabinoid acid during acidification and organic solvent separation. If a high purity metal salt product is desired, then the precipitate should be vacuum dried at low temperature and washed with a hydrocarbon solvent containing a small about of an organic acid, e.g., normal pentane with 0.1 mass % acetic acid.

To yield high purity CBDA, dried $Mg(CBDA)_2$ is washed with the acetic acid/normal pentane solution, removing substantially all color to leave a white solid. The decolorized solid is placed into a vessel with HCl and one or more solvents to aid the acidification and CBDA extraction. The organic layer is vacuum dried at low temperature until a solid CBDA forms in high yield. Rapid solvent expansion of the solid by way of carbon dioxide partial dissolution and rapid depressurization yields a fluffy white powder of greater than 99% purity by NMR and HPLC.

Ultrahigh purity CBD can be made from this CBDA simply by decarboxylation and recrystallization if one so desired. For instance, ultra-high purity materials are desired for producing analytical standards, which command a high market value.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

Definitions:

As used herein, the term "composition" is intended to encompass a product comprising the specified ingredients in the specified amounts, as well as any product which results, directly or indirectly, from combination of the specified ingredients in the specified amounts.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

By "room temperature" it is meant a temperature in the range of about 20 to 25° C. (68-77° F.).

An "isomer" is one of two or more compounds that have the same chemical formula but different arrangements of the atoms within the molecules and that may have different physical/chemical properties.

An "aprotic polar solvent" is a solvent that is polar and lacks an acidic proton. Aprotic polar solvents lack hydroxyl and amine groups. In contrast to protic solvents, these solvents do not serve as proton donors in hydrogen bonding, although they can be proton acceptors. Many solvents, including chlorocarbons and hydrocarbons, are classifiable as aprotic, but polar aprotic solvents are of particular interest for their ability to dissolve salts. Aprotic polar solvents include acetone, acetonitrile, dichloromethane, dimethylformamide (DMF), dimethylpropyleneurea, dimethyl sulfoxide (DMSO), ethyl acetate, hexamethylphosphoramide (HMPA), hexamethylphosphoric triamde (HMPT), pyridine, sulfolane, and tetrahydrofuran (THF).

The word "cannabinoid" as used herein refers to any compound that interacts with cannabinoid receptors including endocannabinoids (produced naturally in the body by humans and animals), phytocannabinoids (found in *cannabis* and some other plants), and synthetic cannabinoids (manufactured artificially). The term "cannabinoid acid" refers to the acid form of the above-mentioned cannabinoids.

The word "cannabidiol" refers to cannabidiol (CBD) and CBD derivatives. CBD may be obtained from industrial hemp extract with a trace amount of THC or from *cannabis* extract using high CBD *cannabis* cultivars. According to some embodiments, cannabidiol may be obtained from plant extract, or may be prepared synthetically (manufactured artificially), the structure of CBD is presented below:

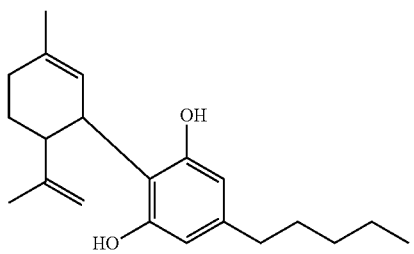 [SMILES: C=C(C)C1CCC(C)=CC1c1c(O)cc(CCCCC)cc1O]

The abbreviation "CBDA" is used herein to refer to the common cannabidiolic acid, which is the acid form of CBD. The term "cannabidiolic acid ester" or "cannabidiolic ester" refers to various molecules, which are the alkyl, alkenyl or alkynyl form of CBDA. The structure of CBDA is presented below:

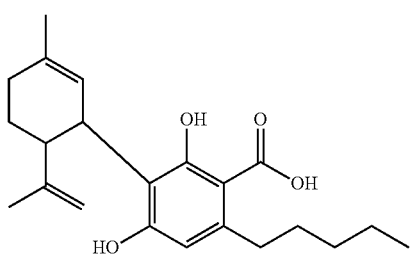 [SMILES: C=C(C)C1CCC(C)=CC1c1c(O)cc(CCCCC)c(C(=O)O)c1O]

The term "extract" as used herein refers a product prepared by extraction by physical means (e.g. by comminuting, pressing, heating, pulsed electric field assisted treatments, shear treatments and pressure wave treatments), by chemical means (e.g. by treatment with an acid, a base, a solvent) and/or by biochemical means (e.g. by treatment with hydrolytic enzymes, microorganisms). The term refers to a liquid substance obtained through extraction from a given substance, or to a concentrate or essence which is free of, or substantially free of solvent. The term extract may be a single extract obtained from a particular extraction step or series of extraction steps. Extract also may be a combination of extracts obtained from separate extraction steps or separate feedstocks. Such combined extracts are thus also encompassed by the term "extract". Any methods of extraction with suitable solvent are encompassed. Exemplary extraction methods can be found for example in U.S. Pat. No. 6,403,126 to Webster and Sarna, the contents of which are incorporated by reference herein. The extract may be obtained from any part of the plait e.g., from leaves, flowers, stems, roots, fruits and seeds. The extract may be aqueous or oily.

It is contemplated that the purity of the cannabinoid starting matter can impact the purity of the final product, especially if its impurities were other cannabinoids, as these likely would be converted to their corresponding cannabinoid acids. Preferably, a purity for the starting CBD (or other cannabinoid depending upon the desired end product) is 98-99% or higher, which is readily available.

According to some embodiments, the *cannabis* plant extract is formed through contact with a suitable solvent or a combination of solvents. According to some embodiments, the solvent is selected from the group consisting of a polar solvent, a hydrocarbon solvent, carbon dioxide, and a combination thereof.

The term "extract" further refers to a liquid or semi-solid or resinous substance obtained through extraction from plants defined in the present application, i.e., extracts obtained from *cannabis* plant e.g., *Cannabis sativa, Cannabis indica*, and *Cannabis ruderalis*. In some embodiments, the term refers to a mixture of liquid or semi-solid, resinous substances obtained through extraction from two or more different plants. In some embodiments, the term refers also to a compound purified from the extract. According to some embodiments, the term "extract" has the meaning of a mixture or combination of two or more extracts.

The term "*cannabis* extract" as used herein refers to one or more plant extracts from the *cannabis* plant. A *cannabis* extract contains, in addition to one or more cannabinoids, one or more non-cannabinoid components which are co-extracted with the cannabinoids from the plant material Their respective ranges in weight will vary according to the starting plant material and the extraction methodology used. Cannabinoid-containing plant extracts may be obtained by various means of extraction of *cannabis* plant material. Such means include but are not limited to supercritical or sub-critical extraction with $CO_2$, extraction with hot or cold gas and extraction with solvents. In some embodiments, the term refers to a mixture of liquid or semi-solid, resinous substances obtained through extraction from two or more different *cannabis* species. In some embodiments, the term refers also to a compound purified from the extract.

The term "*cannabis* plant" as used herein, refers to plants of the genus (*Cannabis*, including but not limited to *Cannabis* saliva, *Cannabis* indica, and *Cannabis ruderalis*. According to some embodiments, *cannabis* plant is a CBD-rich strain of *cannabis* plant or THC-rich strain of *cannabis* plant. Each possibility represents a separate embodiment.

The term "hybrid strain" refers to different strains of *Cannabis* which include differing amounts and/or ratios of the various cannabinoid compounds. For example, *Cannabis sativa* typically has a relatively high THC/CBD ratio. Conversely, *Cannabis* indica has a relative low THC/CBD ratio compared to *Cannabis sativa* (although the absolute amount of THC can be higher in *Cannabis* indica than in *Cannabis sativa*).

As used herein the terms "high-CBD strain" and "CBD-rich strain" refer to a strain of *cannabis* plant which comprises CBD and optionally one or more additional cannabinoids, such as, for example, but not limited to: THC, CBN, and the like. According to some embodiments, CBD is the main component in the high-CBD strain.

The term "THC" as used herein refers to tetrahydrocannabinol. THC is the principal psychoactive constituent of *cannabis* and one of at least 113 total cannabinoids identified in the plant. CBD may be obtained from industrial hemp extract with a trace amount of THC or from *cannabis* extract using high CBD *cannabis* cultivars. According to some embodiments, cannabidiol may be obtained from plant extract, or may be prepared synthetically (manufactured artificially).

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the synthesis and purification of cannabidiolic acid (CBDA) comprising the steps of:
dissolving cannabidiol (CBD) in acetonitrile;
adding 1,8-diazabicyclo[5.4.0]undec-7-ene (DBU) to the dissolved CBD to form a first reaction mixture;
incubating the first reaction mixture at 15 to 25° C. under a pressure of 24 to 36 bar carbon dioxide for about 18 to about 30 hours to form a complex between DBU and CBD;
mixing the DBU-CBD complex with anhydrous magnesium sulfate to form a second reaction mixture comprising $Mg(CBDA)_2$; and
precipitating $Mg(CBDA)_2$ from the second reaction mixture using normal pentane to form a metal salt of CBD.

2. The method for the synthesis and purification of cannabidiolic acid (CBDA) according to claim 1 further comprising the steps of acidifying the metal salt of CBD with hydrochloric acid and precipitating the formed acid with methyl acetate to yield a purified cannabinolic acid.

3. The method for the synthesis and purification of cannabidiolic acid (CBDA) according to claim 2 wherein the acidifying and precipitating steps are performed at about 25° C. or less.

4. The method for the synthesis and purification of cannabidiolic acid (CBDA) according to claim 1 wherein the first reaction mixture is incubated for about 24 hours.

5. A method for the synthesis and purification of a cannabinoid acid (CA) comprising the steps of:
dissolving a cannabinoid in an aprotic polar solvent;
adding a strong base to the dissolved cannabinoid to form a first reaction mixture;
incubating the first reaction mixture at low temperature under pressurized carbon dioxide for a plurality of hours to form a complex between the strong base and the cannabinoid;
mixing the strong base-cannabinoid complex with anhydrous magnesium sulfate to form a second reaction mixture; and
precipitating Mg(cannabinoid)$_2$ from the second reaction mixture using an organic solvent to form a metal salt of the cannabinoid.

6. The method for the synthesis and purification of a CA according to claim 5 further comprising the step of acidifying the metal salt of the cannabinoid with a mineral acid and a third solvent to form a purified CA.

7. The method for the synthesis and purification of a CA according to claim 6 wherein the third solvent is selected from the group consisting of methyl acetate, ethyl acetate, methylene chloride, chloroform, n-pentane, and paraffin solvents.

8. The method for the synthesis and purification of a CA according to claim 6 wherein the mineral acid is selected from the group consisting of hydrochloric acid, sulfuric acid, and nitric acid.

9. The method for the synthesis and purification of a CA according to claim 5 further comprising the step of acidifying the metal salt with HCl and methyl acetate to form a purified CA.

10. The method for the synthesis and purification of a CA according to claim 5 wherein the low temperature is about 15 to about 25° C.

11. The method for the synthesis and purification of a CA according to claim 5 wherein the incubation period is about 18 to about 30 hours.

12. The method for the synthesis and purification of a CA according to claim 5 wherein the incubation period is about 24 hours.

13. The method for the synthesis and purification of a CA according to claim 5 wherein the incubation is performed in a pressure vessel at about 30 bar.

14. The method for the synthesis and purification of a CA according to claim 5 wherein the aprotic polar solvent is acetonitrile.

15. The method for the synthesis and purification of a CA according to claim 5 wherein the aprotic polar solvent is selected from the group consisting of acetone, dichloromethane, dimethylformamide (DMF), dimethylpropyleneurea, dimethyl sulfoxide (DMSO), ethyl acetate, hexamethylphosphoramide (HMPA), hexamethylphosphoric triamide (HMPT), pyridine, sulfolane, and tetrahydrofuran (THF).

16. The method for the synthesis and purification of a CA according to claim 5 wherein an organic solvent is used to precipitate the metal salt and the solvent is selected from the group consisting of normal pentane, normal hexane, methyl acetate, ethyl acetate, and isomers thereof.

17. The method for the synthesis and purification of a CA according to claim 5 wherein the strong base is selected from the group consisting of 1,5,7-Triazabicyclo(4.4.0)dec-5-ene (TBD), 7-Methyl-1,5,7-triazabicyclo(4.4.0)dec-5-ene (MTBD), 1,5-Diazabicyclo[4.3.0]non-5-ene (DBN), and 1,1,3,3-Tetramethylguanidine (TMG).

18. The method for the synthesis and purification of a CA according to claim 5 wherein the first reaction mixture is incubated under pressurized carbon dioxide of at least 2 bar.

19. The method for the synthesis and purification of a CA according to claim 5 wherein the cannabinoid is selected from the group consisting of CBD, CBG, CBN, and THC.

20. A method for the synthesis and purification of a cannabinoid acid comprising the steps of:
dissolving a cannabinoid in an aprotic polar solvent;
adding 1,8-diazabicyclo[5.4.0]undec-7-ene (DBU) to the dissolved cannabinoid to form a first reaction mixture;
incubating the first reaction mixture at low temperature under high pressure carbon dioxide for a plurality of hours to form a complex between DBU and the cannabinoid;
mixing the DBU-cannabinoid complex with anhydrous magnesium sulfate to form a second reaction mixture; and
precipitating Mg(cannabinoid)$_2$ from the second reaction mixture using an organic solvent to form a metal salt of the cannabinoid.

21. The method for the synthesis and purification of a cannabinoid acid according to claim 20 wherein the cannabinoid is selected from the group consisting of CBD, CBG, CBN, and THC.

22. The method for the synthesis and purification of a cannabinoid acid according to claim 20 further comprising the step of acidifying the metal salt of the cannabinoid with a mineral acid and a solvent.

23. The method for the synthesis and purification of a cannabinoid acid according to claim 20 wherein the organic solvent is methyl acetate.

24. The method for the synthesis and purification of a cannabinoid acid according to claim 20 wherein the low temperature is about 15 to 25° C.

25. The method for the synthesis and purification of a cannabinoid acid according to claim 20 wherein the incubation period is about 18 to about 30 hours.

26. The method for the synthesis and purification of a cannabinoid acid according to claim 20 wherein the incubation period is about 24 hours.

27. The method for the synthesis and purification of a cannabinoid acid according to claim 20 wherein the incubation is performed in a pressure vessel at about 24 to 36 bar.

28. The method for the synthesis and purification of a cannabinoid acid according to claim 20 wherein the aprotic polar solvent is acetonitrile.

29. The method for the synthesis and purification of a cannabinoid acid according to claim 20 wherein the organic solvent used to precipitate the metal salt is selected from the group consisting of normal pentane, normal hexane, methyl acetate, ethyl acetate, and isomers thereof.

* * * * *